United States Patent
Sundaram

(10) Patent No.: US 9,572,887 B2
(45) Date of Patent: *Feb. 21, 2017

(54) FORMULATIONS OF BENDAMUSTINE

(71) Applicant: Eagle Pharmaceuticals, Inc., Woodcliff Lake, NJ (US)

(72) Inventor: Srikanth Sundaram, Somerset, NJ (US)

(73) Assignee: EAGLE PHARMACEUTICALS, INC., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/184,464

(22) Filed: Jun. 16, 2016

(65) Prior Publication Data
US 2016/0296621 A1    Oct. 13, 2016

Related U.S. Application Data

(63) Continuation of application No. 14/857,064, filed on Sep. 17, 2015, which is a continuation of application No. 14/714,578, filed on May 18, 2015, now Pat. No. 9,144,568, which is a continuation of application No. 13/838,090, filed on Mar. 15, 2013, now Pat. No. 9,034,908.

(60) Provisional application No. 61/613,173, filed on Mar. 20, 2012, provisional application No. 61/669,889, filed on Jul. 10, 2012.

(51) Int. Cl.
*A61K 31/4184* (2006.01)
*A61K 47/10* (2006.01)
*A61K 9/00* (2006.01)
*A61K 47/20* (2006.01)
*A61K 47/02* (2006.01)
*A61K 47/22* (2006.01)

(52) U.S. Cl.
CPC .......... *A61K 47/10* (2013.01); *A61K 9/0019* (2013.01); *A61K 31/4184* (2013.01); *A61K 47/02* (2013.01); *A61K 47/20* (2013.01); *A61K 47/22* (2013.01)

(58) Field of Classification Search
None
See application file for complete search history.

(56) References Cited

U.S. PATENT DOCUMENTS

| | | |
|---|---|---|
| 4,071,620 A | 1/1978 | Sklar |
| 4,711,906 A | 12/1987 | Von Stetten et al. |
| 5,223,515 A | 6/1993 | Mikura et al. |
| 7,772,274 B1 | 8/2010 | Palepu |
| 8,076,366 B2 | 12/2011 | Courvoisier et al. |
| 8,344,006 B2 | 1/2013 | Drager et al. |
| 8,389,558 B2 | 3/2013 | Alakhov et al. |
| 8,609,707 B2* | 12/2013 | Palepu ............... A61K 31/4184 514/127 |
| 9,000,021 B2 | 4/2015 | Sundaram et al. |
| 9,034,908 B2* | 5/2015 | Sundaram .......... A61K 31/4184 514/394 |
| 9,144,568 B1* | 9/2015 | Sundaram .......... A61K 31/4184 |
| 9,265,831 B2 | 2/2016 | Palepu et al. |
| 2004/0043069 A1 | 3/2004 | Vanderbist et al. |
| 2005/0042285 A1 | 2/2005 | Ukai et al. |
| 2006/0035945 A1 | 2/2006 | Attardo et al. |
| 2006/0128777 A1 | 6/2006 | Bendall et al. |
| 2006/0159713 A1 | 7/2006 | Brittain et al. |
| 2008/0118544 A1 | 5/2008 | Wang |
| 2009/0082416 A1 | 3/2009 | Czarnik |
| 2009/0209606 A1 | 8/2009 | Bendall et al. |
| 2009/0264488 A1 | 10/2009 | Cooper et al. |
| 2009/0325978 A1 | 12/2009 | Onai et al. |
| 2010/0092474 A1 | 4/2010 | Gallagher et al. |
| 2010/0145266 A1 | 6/2010 | Orlowski |
| 2010/0216858 A1 | 8/2010 | Popek et al. |
| 2010/0273730 A1 | 10/2010 | Hsu et al. |
| 2011/0015244 A1 | 1/2011 | Alakhov et al. |
| 2011/0015245 A1 | 1/2011 | Alakhov et al. |
| 2011/0184036 A1* | 7/2011 | Palepu ............... A61K 31/4184 514/394 |
| 2011/0190363 A1* | 8/2011 | Drager .................. A61K 9/08 514/394 |
| 2012/0059000 A1 | 3/2012 | Ren et al. |
| 2012/0071532 A1 | 3/2012 | Cooper et al. |
| 2012/0157505 A1 | 6/2012 | La Bell et al. |
| 2013/0041003 A1 | 2/2013 | Brittain et al. |
| 2013/0041004 A1 | 2/2013 | Drager et al. |
| 2013/0210878 A1* | 8/2013 | Soppimath ............ A61K 47/02 514/394 |
| 2013/0210879 A1* | 8/2013 | Palepu ................... A61K 47/10 514/394 |
| 2013/0253025 A1 | 9/2013 | Sundaram et al. |

(Continued)

FOREIGN PATENT DOCUMENTS

| | | |
|---|---|---|
| CN | 101584668 A | 11/2009 |
| CN | 102164579 A | 8/2011 |

(Continued)

OTHER PUBLICATIONS

U.S. Appl. No. 15/184,464, filed Jun. 2016, Sundaram.*
U.S. Appl. No. 15/008,827, filed Jan. 2016, Sundaram.*
U.S. Appl. No. 14/857,064, filed Sep. 2015, Sundaram.*
U.S. Appl. No. 14/820,291, filed Aug. 2015, Sundaram.*
U.S. Appl. No. 13/767,672, filed Feb. 2014, Palepu.*
Shoffski et al., Weekly administration of bendamustine: A phase I study in patients with advanced progressive solid tumours, Annals of Oncology II: 729-734, 2000.*
Preiss et al., Pharmacological and Clinical Data of Bendamustin, 17th Int'l Cancer Congress, Rio de Janeiro, Brazil, Aug. 24-28, 1998, Ed., Marcos Moraes, and Preiss et al., Pharmacological and Clinical Data of Bendamustin, 17th Int'l Cancer Congress, Rio de Janeiro, Brazil, Aug. 24-28, 1998, Ed., Marcos Moraes, Ricardo Brentani, Ruy Bevilacqua.*

(Continued)

*Primary Examiner* — Svetlana M Ivanova
(74) *Attorney, Agent, or Firm* — Lucas & Mercanti, LLP

(57) ABSTRACT

Methods of treatment using bendamustine formulations designed for small volume intravenous administration are disclosed. The methods conveniently allow shorter administration time without the active ingredient coming out of solution as compared to presently available formulations.

29 Claims, No Drawings

(56) References Cited

U.S. PATENT DOCUMENTS

2014/0094496 A1 4/2014 Sundaram et al.
2014/0275196 A1 9/2014 Sundaram

FOREIGN PATENT DOCUMENTS

| DE | 159289 | 3/1983 |
|---|---|---|
| JP | H09508128 A | 8/1997 |
| JP | 2005537285 A | 12/2005 |
| JP | 2008526991 A | 7/2008 |
| JP | 2012503666 A | 2/2012 |
| JP | 2012525387 A | 10/2012 |
| JP | 2015501814 A | 1/2015 |
| WO | 2010036702 A1 | 4/2010 |
| WO | 2010126676 A1 | 11/2010 |
| WO | 2010148288 A2 | 12/2010 |
| WO | 2011094565 A1 | 8/2011 |
| WO | 2012015810 A2 | 2/2012 |
| WO | 2013142358 A1 | 9/2013 |

OTHER PUBLICATIONS

Biewenga et al., "The Pharmacology of the Antioxidant Lipoic Acid," Gen. Pharmac., vol. 39, No. 3, pp. 315-331 (1997).
Rowe et al., "Handbook of Pharmaceutical Excipients," 6th edition, pp. 454-455 (2009).
Spiegel et al., "Use of Nonaqueous Solvents in Parenteral Products," Journal of Pharmaceutical Sciences, vol. 52, No. 10 pp. 917-927 (1963).
International Search Report and Written Opinion issued in counterpart PCT/US2013/26187 dated May 2013 (2 pages).
Thiesen, "Bendamustine, a well-tollerated cytotoxic agent used in Germany for may years, is soon to be marketed in the rest of Europe for a range of indicatons including chronic lymphocytic leukaemia,"pp. 1-4 (2010). Available at http://www.hospitalpharmacyeurope.com/featured-articles/bendamustine.
Preiss et al., "Pharmacological and clinical date of Bendamustine," 17th International Cancer Congress, pp. 1637-1640 (1998).
Schoffski et al., "Weekly administration of bendamustine: A phase 1 study in patients with advanced progressive solid tumors," Annals of Oncology II, pp. 729-734 (2000).
Rassachaert et al., "A phase 1 study of bendamustine hydrochloride administered once every 3 weeks in patients with solid tumors," Anti-Cancer Drugs, vol. 18 No. 5 pp. 587-595 (2007).
Schoffski et al., Repeated administration of short infusions of bendamustine: a phase 1 study in patients with advanced progressive solid tumours, J. Cancer Res Clin Oncol, vol. 126 No. 1 pp. 41-47 (2000).
Treanda, "Highlights of Prescribing Information," TREANDA ( bendamustine hydrochloride) for Injection, for intravenous infusion, pp. 1-13 (2010).
Zips et al., "New Anticancer Agents: In Vitro and In Vivo Evaluation," In Vivo,vol. 19 pp. 1-8 (2005).
Sikora, "Cancer drug development in the post-genomic age," Current Science, vol. 81 No. 5 pp. 549-554 (2001).
International Search Report and Written Opinion issued in counterpart PCT/US2013/032295 dated Jun. 2013 (4 pages).
International Search Report and Written Opinion of International application based on PCT/US2011/022958, dated Apr. 2011 (8 pages).
Third Party Submission in related EP2528602 based on PCT/US2011/022958 dated Nov. 2013.
Supplementary European Search Report in related EP 2528602 dated Jan. 2014.
Maas et al., "Stabilitat von Bendamustinhydrochlorid in Infusionslosungen," Die Pharmazie, Govi Verlag Pharmazeutishcher Verlag GmbH, vol. 49. No. 10 pp. 775-777 (1994). (Abstract Only).
International Search Report and Written Opinion for No. PCT/US2013/032289 dated Jun. 2013.
Sigma-Aldrich, Webpage Catalog for poly(ethylene glycol), http://www.sigmaaldrich.com/catalog/product/aldrich/202398?lang=en&region=US#, accessed Nov. 15, 2015 (2 pages).

* cited by examiner

FORMULATIONS OF BENDAMUSTINE

CROSS-REFERENCE TO RELATED APPLICATIONS

This application is a continuation of copending U.S. application Ser. No. 14/857,064, filed Sep. 17, 2015, which is a continuation of U.S. application Ser. No. 14/714,578, filed May 18, 2015, now U.S. Pat. No. 9,144,568, which is a continuation of U.S. application Ser. No. 13/838,090, filed Mar. 15, 2013, now U.S. Pat. No. 9,034,908, issued May 19, 2015, which in turn claims the benefit of priority from U.S. Provisional Patent Application Ser. No. 61/613,173, filed Mar. 20, 2012, and 61/669,889, filed Jul. 10, 2012, the disclosure of each of which is incorporated herein by reference.

BACKGROUND OF THE INVENTION

Bendamustine is used in the treatment of a number of cancers including leukemias, Hodgkin's disease and multiple myelomas. Bendamustine (present as the HCl salt) is the active ingredient of the commercial product Treanda™, a lyophilized powder for reconstitution. Current labeling requirements call for the reconstituted product to be immediately (within 30 minutes) diluted into 500 mL of parenterally acceptable diluents such as 0.9% saline (normal saline) or 2.5% dextrose/0.45% saline and administered as part of an intravenous infusion delivering 100 mg/m$^2$ over 30 minutes or 120 mg/m$^2$ over 60 minutes. The diluted admixture may be stored at 2-8° C. for up to 24 hours, or 3 hours at room temperature (15-30° C.); administration must be completed within this period due to limited chemical stability in aqueous solutions.

Solubility limitations at 2-8° C. with currently approved and/or available formulations are believed to prevent current formulations from being administered in smaller more concentrated infusion volumes up to about 150 ml; at volumes below 150 ml, solubility is not sufficient even at 25° C. Side effects associated with extravasation and local erythema, swelling and pain at the injection site also dictate that the infusion be as dilute as possible. Therefore, precautions are taken to avoid extravasation, including monitoring of the intravenous infusion site for redness, swelling, pain, infection, and necrosis during and after administration of bendamustine. Higher infusion volume and longer infusion times, however, are associated with many drawbacks. For example, after reconstitution, the current product has a short period of stability, degradation of the drug occurs from the time of reconstitution until the entire large volume infusion has been completely administered. The current label for Treanda™ therefore instructs that the admixture should be prepared as close as possible to the time of patient administration, and that administration of Treanda™ must be completed within the durations indicated above. From patient comfort and nursing administration points of view, higher infusion volumes and long infusion times are undesirable. Higher infusion volumes may be associated with higher likelihood of weight gain and edema. Shorter infusion times and smaller infusion volumes result in a better quality of life experience for the patient by reducing the overall "stress" to the patient and reducing the time spent in the infusion clinic. Shorter infusion times (and smaller volumes) also reduce the potential extravasation (and shorten the patient monitoring time required). It would be advantageous if the drug could be administered in smaller volumes and over shorter times. The present invention addresses these needs.

SUMMARY OF THE INVENTION

In a first aspect of the invention there are provided methods of treating or preventing cancer or malignant disease in a subject such as a human. The methods include parenterally administering a volume of about 325 ml or less of a liquid composition containing:
  a) from about 0.05 to about 12.5 mg/ml of bendamustine or a pharmaceutically acceptable salt thereof;
  b) a solubilizer comprising polyethylene glycol and propylene glycol; and optionally
  c) a parenterally acceptable diluent; over a substantially continuous period of less than or equal to about 30 minutes to a subject in need thereof.

In alternative aspects of the invention there are provided methods of treating or preventing a bendamustine-responsive condition in a subject such as a human. In a first embodiment the methods include administering less than or equal to 325 ml of a liquid composition which contains

| Ingredient | Concentration Range (mg/ml) |
| --- | --- |
| Bendamustine HCl | 0.05 to 1.6 |
| Solubilizer 1 propylene glycol | 0.30 to 6.5 |
| Solubilizer 2 PEG 400 | 3.3 to 65 |
| Monothioglycerol | 0.02 to 0.35 |
| NaOH | 0.0 to 0.01 | over a substantially continuous period of less than or equal to about 30 minutes to a subject in need thereof.

In a related second embodiment of this aspect of the invention, the methods include administering less than or equal to 325 ml of a liquid composition which contains

| Ingredient | Concentration Range (mg/ml) |
| --- | --- |
| Bendamustine HCl | 1.1 to 12.5 |
| Solubilizer 1 propylene glycol | 4.5 to 51 |
| Solubilizer 2 PEG 400 | 45 to 500 |
| Monothioglycerol | 0.2 to 2.5 |
| NaOH | 0.0 to 0.04 | over a substantially continuous period of less than or equal to about 30 minutes to a subject in need thereof.

The methods of the present invention take advantage of the fact that the concentration of the bendamustine HCl is below the room temperature solubility limit of the vehicle into which it is placed. As a result, the bendamustine does not precipitate during administration to the patient thereby substantially avoiding the side effects which would otherwise occur during small volume administration of therapeutic doses of the drug. In addition, patients or subjects with bendamustine-responsive conditions can be treated using substantially smaller parenteral volumes which are well below the standard 500 ml administration volume.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

In a first aspect of the invention there are provided methods of treating or preventing cancer or malignant disease in a subject or patient who is preferably a human. The methods generally include parenterally administering a volume of about 325 ml or less of a liquid composition containing:

a) from about 0.05 to about 12.5 mg/ml of bendamustine HCl or a pharmaceutically acceptable salt thereof, the HCl salt being preferred;

b) a solubilizer comprising polyethylene glycol and propylene glycol; and optionally c) a parenterally acceptable diluent;

over a substantially continuous period of less than or equal to about 30 minutes to a subject in need thereof.

The solubilizer portion of the formulation preferably includes from about 0.3 to about 45% volume polyethylene glycol (PEG) and from about 0.03 to about 5% volume propylene glycol (PG), as calculated on the basis of the total or final volume administered. Stated alternatively, the final concentration of the PEG generally ranges from about 3 to about 500 mg/ml, while the final concentration of the PG generally ranges from about 0.5 to about 51 mg/ml. Within these general ranges, certain aspects of the invention include concentration ranges for the PEG of from about 45 to about 500 mg/ml or from about 3.3 to about 63.3 mg/ml; and for the PG ranges of from about 4.7 to about 50.6; or from about 0.02 to about 6.5 mg/ml.

In some aspects of the invention, the bendamustine is administered intravenously as part of an intravenous infusion. Contemplated infusion volumes are preferably less than 325 ml with volumes such as about 250 ml, 100 ml, and 50 ml, with each volume varying about +/−10% or +/−15% being preferred in some embodiments. In alternative aspects of the invention, the intravenous administration volume is suitable for IV bolus administration and may also include an amount of pharmaceutically acceptable diluent such as normal saline or one of the other diluents described herein which does not cause the solubility of the vehicle to fall below the concentration of the bendamustine. Stated alternatively, the final concentration of the bendamustine will be below the solubility of the combination vehicle containing the mixture of propylene glycol and PEG and diluent. While most aspects of the invention are described in the context of administering less than about 325 ml including all vehicle ingredients, excipients, etc., it should be appreciated that volumes as low as a few milliliters, e.g. about 2, can be used so long as the vehicle includes sufficient solubilizers to preserve the solubility of the bendamustine therein during administration to the patient.

For purposes of the present invention, the word "about" when used to modify infusion volumes or concentrations shall be understood to include values which may vary by amounts of about +/−10% or 15%. In certain embodiments where the infusion volume is about 50 ml, the concentration of the bendamustine HCl or other pharmaceutically acceptable salt thereof is preferably from about 0.5 to about 5.6 mg/ml. In embodiments where the infusion volume is about 100 ml, the concentration of the bendamustine HCl or other pharmaceutically acceptable salt thereof can be preferably from about 0.1 to about 3.2 mg/ml. Similarly, in some aspects of the invention where the infusion volume is about 250 ml, the concentration of the bendamustine HCl or other pharmaceutically acceptable salt thereof is from about 0.05 to about 1.4 mg/ml.

The solubilizer is preferably a mixture of polyethylene glycol, hereinafter "PEG" and propylene glycol, hereinafter "PG". The solubilizer can also optionally include an antioxidant such as monothioglycerol. The amount of antioxidant included is a formulation stabilizing amount, which, in the case of monothioglycerol ranges from about 2 to about 10 mg/ml. The PEG preferably has a molecular weight of about 400, i.e. PEG 400. Other molecular weight PEG's known to those of ordinary skill can be included if desired in alternative embodiments.

Certain aspects of the invention call for the ratio of the PEG to PG found in the solubilizer to be about 90:10. In alternative aspects, the ratio of the PEG to PG is about 85:15.

In some aspects of the invention, the total amount of solubilizer, i.e. blend of PEG and PG, included in infusion volumes of about 100-115 ml is from about 0.5 to about 26.5% vol.; while amounts of from about 0.2 to about 5% vol. for the solubilizer are preferably included in infusion volumes of about 250-265 ml; with solubilizer amounts of from about 2.0 to about 22.4% vol. included in infusion volumes of about 50-65 ml.

Since the solubilizer is a blend, the amount of PEG and PG in various volumes (calculated as % vol.) can be as follows:

| Solubilizer | 50 ml | 100 ml | 250 ml |
| --- | --- | --- | --- |
| PEG | 20.12 | 11.33 | 4.9 |
| PG | 2.24 | 1.26 | 0.54 |

In some preferred embodiments, the methods of the invention are advantageously carried out using bendamustine HCl containing compositions administered as small volume infusions with volumes of about 50 ml or about 100 ml or about 250 ml. Such smaller volumes allow the drug to be administered over a time period of about 10 minutes or less as part of an intravenous infusions containing a volume of about 50 ml; about 15 minutes or less as part of an intravenous infusions containing a volume of about 100 ml or when volumes of about 250 ml are infused, the IV infusion is administered over a time period of about 30 minutes or less. Depending upon the amount of drug administered, the IV bolus volumes containing sufficient amount of the drug will be less than 50 ml, with amounts of about 10 or 15 to 30 ml being sufficient.

The infusible compositions in many aspects of the invention will also preferably include the parenterally acceptable diluents such as water for injection (WFI), 0.9% saline (normal saline, preferred), 0.45% saline (half normal saline) or 2.5% dextrose/0.45% saline. Formulations well suited for carrying out the methods described herein are also described in commonly assigned US Published Patent Application Nos. 2011/0184036, filed Jan. 28, 2011, and 2013/0210879 filed Feb. 14, 2013, the contents of which are incorporated herein by reference. As reviewed in the '672 patent application, some preferred bendamustine formulations can also include a minor amount of a pH adjuster such as sodium formate, sodium phosphate, potassium hydroxide, phosphoric acid or, preferably, sodium hydroxide.

In an alternative embodiment of the invention, the bendamustine formulations used in the methods described herein can be one or more of those described in U.S. Pat. Nos. 8,344,006 and 8,076,366; and US Published Patent Application Nos. 2013/0041004; 2012/0071532; 2010/0216858; 2006/0159713; and 2013/0041003, the contents of each of which are incorporated herein by reference. It being understood that the vehicle into which the bendamustine HCl is placed will have sufficient bendamustine solubility which exceeds the concentration of the drug included therein.

For example, 2011/0184036 discloses long term storage stable bendamustine-containing compositions including:
 a) bendamustine or a pharmaceutically acceptable salt thereof; and
 b) a pharmaceutically acceptable fluid including
  i) PEG, PG or mixtures thereof; and
  ii) a stabilizing amount of an antioxidant.

The total impurities in the inventive compositions resulting from the degradation of the bendamustine in the compositions is less than about 5% PAR as determined by HPLC at a wavelength of 223 nm after at least about 15 months at a temperature of from about 5° C. to about 25° C., and thus have long term stability for at least the same period of time or longer. Preferably, the bendamustine-containing compositions demonstrate long term storage stability for at least about 2 years, especially when stored at the lower (refrigerated) temperatures. In one embodiment, the amount of total impurities in the inventive compositions resulting from the degradation of the bendamustine is less than about 3% PAR as determined by HPLC at a wavelength of 223 nm after at least about 2 years at a temperature of from about 5° C. to about 25° C.

In some aspects of the invention, the bendamustine concentration in the inventive compositions is from about 10 mg/mL to about 100 mg/mL, preferably 20 mg/mL to about 60 mg/mL. Preferably the bendamustine concentration in the inventive compositions is from about 25 mg/mL to about 50 mg/mL, and more preferably from about 30 mg/mL to about 50 mg/mL. It will be understood that compositions containing any useful concentration within the ranges, i.e. 10, 20, 25, 30, 35, 40, 45, 50, 55, 60 . . . 100 are contemplated. In other embodiments, the bendamustine concentration in the composition is about 50 mg/mL. In alternative aspects, the amount of bendamustine is outside these ranges but the amounts will be sufficient for single or multiple administrations of dosages generally regarded as effective amounts.

In several embodiments of the invention, pharmaceutically acceptable fluid is non-aqueous and may be, but is not necessarily, a solvent for the bendamustine or salt thereof. Within this aspect, the pharmaceutically acceptable fluid is propylene glycol (PG) or polyethylene glycol (PEG). In other embodiments of the invention however, the pharmaceutically acceptable fluid is a mixture of PEG and PG. For example, the pharmaceutically acceptable fluid can include about 50% PEG and about 50% PG. Alternatively, pharmaceutically acceptable fluid includes about 95% PEG and about 5% PG. The amount of PEG and PG can also be varied within the ranges, i.e. the ratio of PEG:PG in the pharmaceutically acceptable fluid can range from about 95:5 to about 50:50. Within this range, is a pharmaceutically acceptable fluid containing about 75% PEG and about 25% PG, and preferably 80% PEG and 20% PG. In another embodiment, a pharmaceutically acceptable fluid can include about 85% PEG and about 15% PG while another preferred pharmaceutically acceptable fluid includes about 90% PEG and about 10% PG. The molecular weight of the PEG will be within the range of pharmaceutically acceptable weights although PEG 400 is preferred in many aspects of the invention.

Without meaning to be bound by any theory or hypothesis, the hydroxide of the polyethylene glycol molecule is less reactive than the hydroxides of propylene glycol. As a result, the ester forms at a slower rate in polyethylene glycol than propylene glycol and the resulting bendamustine degradants are unexpectedly and substantially reduced over extended periods of time when PEG is a substantial part of the pharmaceutically acceptable fluid.

The bendamustine-containing compositions according to several preferred aspects of the invention include a stabilizing amount of an antioxidant. For purposes of the present invention, "stabilizing amount" shall be understood to include those amounts which increase or enhance the stability of the bendamustine in the compositions described herein. The presence of one or more antioxidants described herein thus contributes, at least in part to the long term stability of the composition. Within this guideline, suitable antioxidant concentrations in the compositions can range from about 2.5 mg/mL to about 35 mg/mL, and preferably from about 5 mg/mL to about 20 mg/mL or from about 10 mg/mL to about 15 mg/mL. In some other embodiments, the concentration of the antioxidant in the bendamustine-containing composition is about 5 mg/mL.

Suitable antioxidants for inclusion include those which are pharmaceutically acceptable for use in human and veterinary formulations although not limited to those currently regarded as safe by any regulatory authority. For example, the antioxidant can be selected from among lipoic acid, thioglycerol (also known as monothioglycerol) and analogs thereof, propyl gallate, methionine, cysteine, metabisulfites, sodium formaldehyde sulfoxylate, phenol-containing aromatic and aliphatic compounds, dihydrolipoic acid and mixtures of the foregoing. Preferably, the antioxidant is thioglycerol, lipoic acid or a mixture thereof. Some particularly preferred embodiments of the invention include thioglycerol.

In view of the foregoing, some preferred long term storage stable bendamustine-containing compositions in accordance with the invention compositions include:
 I. a) bendamustine or a pharmaceutically acceptable salt thereof; and
  b) a pharmaceutically acceptable fluid including
   i) polyethylene glycol and propylene glycol; and
   ii) a stabilizing amount of thioglycerol; or
 II. a) about 50 mg/mL bendamustine or a pharmaceutically acceptable salt thereof; and
  b) a pharmaceutically acceptable fluid including
   i) about 90% PEG and about 10% PG; and
   ii) about 2.5 mg/mL thioglycerol.

Each of these compositions have the same stability profiles already described, i.e. having less than about 5% total impurities, PAR as determined by HPLC at a wavelength of 223 nm, after at least about 15 months of storage at a temperature of from about 5° C. to about 25° C.

In accordance with other aspects of the invention, there are provided long term storage stable bendamustine-containing compositions, including:
 a) bendamustine or a pharmaceutically acceptable salt thereof;
 b) a pharmaceutically acceptable fluid including one or more of the following: PG, ethanol, PEG, benzyl alcohol and glycofurol; and
 c) a stabilizing amount of a chloride salt.

These compositions also have the low levels of impurities and long term stability mentioned herein. Preferred pharmaceutically acceptable fluids include PG, PEG or ethanol in this embodiment of the invention. Preferably, the PEG is PEG 400. If desired, glycerin and/or 88% (w/w) lactic acid can be added to the pharmaceutically acceptable fluid.

Suitable chloride salts include but are not limited to organic chloride salts, sodium chloride, choline chloride, hydrochloride salts of amino acids and mixtures thereof. Thus, as will be appreciated by those of ordinary skill, one can select from among a number of suitable chloride salts and it is Applicants' intention that the scope of the invention includes all such chloride salts that are capable of being included in bendamustine-containing formulations for extended periods without having a deleterious effect on the drug. In one embodiment of the invention, the chloride salt concentration is from about 10 to about 300 mg/mL. In another embodiment, the chloride salt concentration is from about 50 to about 215 mg/mL. In one preferred embodiment, the chloride salt concentration is about 215 mg/mL.

In accordance with another aspect of the invention, there is provided long term storage stable bendamustine-containing compositions, including:

a) bendamustine or a pharmaceutically acceptable salt thereof; and b) a pharmaceutically acceptable fluid including DMSO.

These compositions also have the low levels of impurities and long term stability mentioned herein. In some aspects, the bendamustine concentration in these compositions is from about 10 mg/mL to about 100 mg/mL. Preferably, the bendamustine concentration is from about 20 mg/mL to about 50 mg/mL, more preferably from about 25 mg/mL to about 50 mg/mL. In an alternative embodiment, the bendamustine concentration is about 50 mg/mL.

In a further aspect of the invention, there are provided methods of controlling or preventing the formation of impurities in bendamustine-containing compositions during long term storage. The methods include combining an amount of bendamustine or a pharmaceutically acceptable salt thereof with a sufficient amount of a pharmaceutically acceptable fluid containing one of the following:

A) i) PEG, PG or mixtures thereof; and
  ii) a stabilizing amount of an antioxidant;

B) i) one or more of PG, ethanol, PEG, glycofurol and benzyl alcohol; and
  ii) a stabilizing amount of a chloride salt; or

C) DMSO.

If desired, a sufficient amount of a concentrated, ready to use liquid formulation such one containing 25 mg/ml bendamustine HCl and already admixed with sufficient solubilizers can be transferred to a suitable fixed volume diluent container such as a bag containing 50, 100, 250 ml normal saline or the like. Alternatively, lyophilized bendamustine HCl can be reconstituted, combined with sufficient solubilizer blends as described herein and administered in accordance with the inventive methods. In such embodiments, the actual amount delivered to the patient will be slightly more than the diluent amount so as to allow for the addition of the drug/solubilizer vehicle.

In some aspects of the invention, there are provided methods of treating or preventing chronic lymphocytic leukemia (CLL). The small volume infusions can be given as part of any treatment protocol for which bendamustine is included. Thus, the compositions described herein can be administered as part of a poly-pharmaceutical treatment regimen according to known protocols with the exception that the concentrated bendamustine compositions described herein are administered in smaller infusion volumes over significantly shorter administration periods. For example, some CLL treatment regimens can include administering the compositions described herein intravenously as part of about 100 ml infusions in about 20 minutes or less and more preferably in about 15 minutes or less on days 1 and 2 of a 28 day cycle and repeating the cycle up to 6 times or longer if clinically appropriate. If 250 ml volumes are used to deliver the bendamustine, the time of administration is preferably about 30 minutes or less. If 50 ml volumes are used to deliver the bendamustine, the time of administration is preferably about 10 minutes or less.

In spite of the smaller volumes, the amount of bendamustine HCl administered to the patient in need thereof per dose (infusion or otherwise) in some preferred embodiments is about 100 mg/m$^2$. In some alternative aspects of the invention, the amount of bendamustine HCl administered to the patient in need thereof as part of the 50, 100 or 250 ml infusion is an amount sufficient to provide a dosage of 50 or 25 mg/m$^2$. Additional administration dosages will be apparent to those of ordinary skill based upon clinical experience, patient need without undue experimentation.

In other aspects of the invention, there are methods of treating or preventing the malignant disease of indolent B-cell non-Hodgkin's lymphoma. In these aspects, the composition is administered intravenously as a 100 ml infusion in less than 20 minutes and more preferably in about 15 minutes or less on days 1 and 2 of a 21 day cycle for up to 8 cycles or longer if clinically appropriate. If 250 ml volumes are used to deliver the bendamustine, the time of administration is preferably about 30 minutes or less. If 50 ml volumes are used to deliver the bendamustine, the time of administration is preferably about 10 minutes or less. The amount of bendamustine administered to the subject is preferably about 120 mg/m$^2$, although in alternative embodiments, the amount administered ranges from about 90 or 60 mg/m$^2$. As will be appreciated, further alternative dosage amounts will be apparent to those of ordinary skill based upon clinical experience, patient need without undue experimentation.

It will be appreciated by those skilled in the art that the above-mentioned dosages calculated in mg/m$^2$ for purposes of body surface area (BSA) are consistent with the bendamustine HCl concentrations also described herein, e.g. 0.5 to 5.6 mg/ml. In the alternative, the invention also contemplates IV bolus administration of bendamustine-containing formulations in volumes which can be administered via syringe, e.g. from a few milliliters up to about 50 milliliters, with therapeutic amounts of the drug in a concentration which does not exceed the vehicle solubility for the drug therein.

Further embodiments of the invention include methods of treating or preventing a bendamustine-responsive condition in a subject such as a human. In a first embodiment, the methods include administering less than or equal to 325 ml of a liquid composition which contains

| Ingredient | Concentration Range (mg/ml) |
| --- | --- |
| Bendamustine HCl | 0.05 to 1.6 |
| Solubilizer 1 propylene glycol | 0.30 to 6.5 |
| Solubilizer 2 PEG 400 | 3.3 to 65 |
| Monothioglycerol | 0.02 to 0.35 |
| NaOH | 0.0 to 0.01 | over a substantially continuous period of less than or equal to about 30 minutes to a subject in need thereof. More preferably, the administration time is well below 30 minutes and the administration time will decrease as the volume administered decreases.

Bendamustine formulations containing the above ingredients are capable of delivering approximately 25 mg of the drug as the HCl salt in volumes of pharmaceutically acceptable diluent ranging from about 325 ml down to about 15 ml. For example, 1 ml of a bendamustine HCl ready to use liquid available from Eagle Pharmaceuticals containing

| Ingredient | Concentration (mg/ml) |
|---|---|
| Bendamustine HCl | 25 |
| PG | 103.2 |
| PEG 400 | 1013.4 |
| Monothioglycerol | 5 |
| NaOH | 0.08 | is combined with 300 ml of a normal saline diluent to provide a final IV infusion containing 301 ml and a bendamustine final concentration of 0.08 mg/ml.

One ml of the 25 mg/ml Eagle bendamustine HCl is diluted into additional diluent volumes as shown below:

| Diluent Volume (ml) | Final Volume (ml) | Final Bendamustine Conc. (mg/ml) |
|---|---|---|
| 200 | 201 | 0.12 |
| 100 | 101 | 0.25 |
| 50 | 51 | 0.49 |
| 30 | 31 | 0.81 |
| 15 | 16 | 1.56 |

The measured solubility of the bendamustine HCl in the diluent/solubilizer combination (50 ml diluent plus 1 ml of 25 mg/ml bendamustine HCl and solubilizers, etc.) at room temperature was 10.5 mg/ml using normal saline and 14.2 mg/ml using half normal saline/dextrose. The solubility of the diluent/solubilizer combination far exceeded the bendamustine concentration, thus assuring the avoidance of precipitated drug prior to or during administration. As will be appreciated by those of ordinary skill, as the concentration of solubilizers increases with respect to the total volume in small administration doses, the solubility of the bendamustine is maintained.

In a related second embodiment of this aspect of the invention, the methods include administering less than or equal to 325 ml of a liquid composition which contains

| Ingredient | Concentration Range (mg/ml) |
|---|---|
| Bendamustine HCl | 1.1 to 12.5 |
| Solubilizer 1 propylene glycol | 4.5 to 51 |
| Solubilizer 2 PEG 400 | 45 to 500 |
| Monothioglycerol | 0.2 to 2.5 |
| NaOH | 0.0 to 0.04 | over a substantially continuous period of less than or equal to about 30 minutes to a subject in need thereof. As was the case above, the administration time will decrease with the decrease in volume administered.

Bendamustine formulations containing the above ingredients are capable of delivering approximately 360 mg of the drug as the HCl salt in volumes of pharmaceutically acceptable diluent ranging from about 325 ml down to about 15 ml. As was the case above, the measured solubility of the bendamustine HCl in the diluent/solubilizer combination (1 ml drug+solubilizers, etc. and 50 ml diluent) at room temperature was 10.5 mg/ml using normal saline and 14.2 mg/ml using half normal saline/dextrose.

Instead of using only 1 ml of the above described Eagle 25 mg/ml bendamustine HCl ready to use liquid, 14.4 ml is combined with various amounts of diluent.

| Diluent Volume (ml) | Final Volume (ml) | Final Bendamustine Conc. (mg/ml) |
|---|---|---|
| 300 | 314.4 | 1.15 |
| 200 | 214.4 | 1.68 |
| 100 | 114.4 | 3.15 |
| 50 | 64.4 | 5.59 |
| 30 | 44.4 | 8.11 |
| 15 | 29.4 | 12.24 |

In each case, the solubility of the diluent/solubilizer combination exceeds the bendamustine concentration, thus assuring the avoidance of precipitated drug prior to or during administration.

EXAMPLES

The following examples serve to provide further appreciation of the invention but are not meant in any way to restrict the effective scope of the invention.

Example 1

The solubility of bendamustine HCl, obtained from two different sources, in 0.9% saline and 0.9% saline containing from different amounts of a non-aqueous solubilizer comprising a mixture of polyethylene glycol 400 and propylene glycol (in the volume proportion of 90:10) with and without 5 mg/ml monothioglycerol was determined at both room temperature (22-23° C.) and at refrigerated temperature (5° C.). Essentially, an excess of bendamustine HCl was added to solvents comprising of various volume percent of the non-aqueous solubilizer in 0.9% saline, and allowed to equilibrate with shaking for 30 minutes at room temperature, or for 24 hours at refrigerated temperature. At the end of the equilibration step, the suspensions were filtered through a 0.2 micron filter to remove undissolved bendamustine, and the filtrate solutions analyzed for bendamustine HCl content using a HPLC assay; quantification was performed against a bendamustine HCl reference standard. The solubility data are presented in Table 1.

TABLE 1

Solubility of bendamustine HCl in 0.9% saline with various amounts of non-aqueous solubilizer (90:10 PEG400:PG with and without 5 mg/mL monothioglycerol (MTG))

| | | | Solubility of bendamustine HCl (mg/mL) in 90:10 PEG 400/PG | | |
|---|---|---|---|---|---|
| | Volume % of | Volume % of Non- | Room temperature | | 5° C. |
| Dilution Fold | Normal Saline | aqueous Solubilizer | API Source A | API Source B* B | API Source A |
| n/a | 100.0 | 0.0 | 3.461 | 3.304 | 1.175 |
| 40 | 97.5 | 2.5 | 3.987 | 3.889 | nd |
| 20 | 95.0 | 5.0 | 4.429 | 4.204 | 2.022 |
| 13.3 | 92.5 | 7.5 | nd | 4.742 | nd |
| 10 | 90.0 | 10.0 | 5.626 | 5.351 | 2.431 |
| 8 | 87.5 | 12.5 | nd | 5.825 | nd |
| 6.7 | 85.0 | 15.0 | 7.012 | 6.554 | 2.900 |
| 5.7 | 82.5 | 17.5 | nd | 7.641 | 3.328 |
| 5 | 80.0 | 20.0 | 8.642 | 8.492 | 3.824 |
| 3.3 | 70.0 | 30.0 | 12.006 | 11.407 | nd |

*solvent also contained 5 mg/ml monothioglycerol
nd = not determined;
API = active pharmaceutical ingredient

Example 2

Bendamustine-containing compositions are prepared by adding 5 mg/ml of thioglycerol to a mixture containing 90% polyethylene glycol 400 and 10% propylene glycol. As indicated in the Table 2 below, NaOH may be added to the PEG in an amount sufficient to get apparent pH of greater than or equal to 6.5 as measured using the pH method outlined in the USP monograph for polyethylene glycol (PEG). Bendamustine (BDM) is then added to the sample to a concentration of 10 mg/ml.

TABLE 2

| Formulation |
| --- |
| BDM - 10 mg/mL |
| Thioglycerol - 5 mg/mL |
| PEG 400:PG (90:10) |
| qs to 1 mL |
| BDM - 10 mg/mL |
| Thioglycerol - 5 mg/mL |
| PEG 400:PG (90:10) |
| qs to 1 mL |
| (PEG 400 Treated with NaOH) |

The compositions are then admixed with normal saline based on the total dose of bendamustine HCl, which in turn is based on the patient body surface area (BSA) and the dosing regimen (100 mg/m$^2$ for CLL and 120 mg/m$^2$ for NLL; although dose modifications of 90, 60, 50, and 25 mg/m$^2$ are possible, only the highest two dosing regimens are considered for illustrative purposes, as these result in the highest concentration of bendamustine during infusion). The 100 ml infusion is then made by admixing the dose appropriate volume of the 10 mg/ml solution with a 100 ml portion of normal saline to provide an infusible composition containing the appropriate dose of bendamustine (as the HCl salt) in the final admixture, which can be administered intravenously over about 15 minutes to a patient in need thereof.

As seen in Table 3, the concentrations of bendamustine (as HCl salt) and the corresponding volume percent of non-aqueous component are well below the corresponding solubilities at both room temperature and refrigerated temperature as detailed in Table 1. For example, for a 2.0 m$^2$ (average) patient dosed at 120 mg/m2, the final concentration of bendamustine HCl in a 100 ml admixture is 1.94 mg/mL. This is above the solubility of bendamustine HCl at refrigerated storage conditions in the absence of any non-aqueous components (1.175 mg/ml as shown in Table 1 for 100% normal saline), as would be the case with the currently approved Treanda™ product, thereby precluding preparation and storage of a 100 ml admixture volume at refrigerated conditions. However, the use of the non-aqueous bendamustine formulation described in this example results in the presence of 19.4% of the non-aqueous component in the final admixture, which improves the solubility to about 3.8 mg/mL (solubility of 3.824 mg/mL at 2-8° C. with 20% non-aqueous component, as shown in Table 1). Therefore, the solubility with the non-aqueous formulation is well above the final concentration (of bendamustine HCl) of 1.94 mg/mL, allowing preparation and storage of the 100 ml admixture at refrigerated conditions. In this example, the room temperature solubilities in 100% normal saline and 80% normal saline (with 20% non-aqueous component) are about 3.3 mg/ml and 8.5 mg/ml, respectively (see Table 1), which are also well above the final concentration of 1.94 mg/ml. Therefore, 100 ml admixtures of the non-aqueous formulation described in the example may also be prepared and stored at room temperature. In addition, the non-aqueous formulation of bendamustine described in this example at Table 2 may be diluted into smaller infusion volumes ranging from 250 ml or less, and stored at either room temperature or refrigerated temperature, with bendamustine continuing to remain in solution for extended periods of time as compared to currently available formulations.

TABLE 3

Concentrations of bendamustine (BDM, as HCl salt) and corresponding volume % of non-aqueous (NA) component in the final admixture, for volumes ranging from 100 ml to 250 ml For 10 mg/mL Formulation

| | Admix. Volume 250 mL | | | | Admix. Volume 200 mL | | | |
| --- | --- | --- | --- | --- | --- | --- | --- | --- |
| | 100 mg/m$^2$ dose | | 120 mg/m$^2$ dose | | 100 mg/m$^2$ dose | | 120 mg/m$^2$ dose | |
| BSA (m$^2$) | BDM Conc (mg/ml) | % NA comp. | BDM Conc (mg/ml) | % NA comp. | BDM Conc (mg/ml) | % NA comp. | BDM Conc (mg/ml) | % NA comp. |
| 1.00 | 0.38 | 3.8 | 0.46 | 4.6 | 0.48 | 4.8 | 0.57 | 5.7 |
| 1.25 | 0.48 | 4.8 | 0.57 | 5.7 | 0.59 | 5.9 | 0.70 | 7.0 |
| 1.50 | 0.57 | 5.7 | 0.67 | 6.7 | 0.70 | 7.0 | 0.83 | 8.3 |
| 1.75 | 0.65 | 6.5 | 0.77 | 7.7 | 0.80 | 8.0 | 0.95 | 9.5 |
| 2.00 | 0.74 | 7.4 | 0.88 | 8.8 | 0.91 | 9.1 | 1.07 | 10.7 |
| 2.25 | 0.83 | 8.3 | 0.97 | 9.7 | 1.01 | 10.1 | 1.19 | 11.9 |
| 2.50 | 0.91 | 9.1 | 1.07 | 10.7 | 1.11 | 11.1 | 1.30 | 13.0 |
| 2.75 | 0.99 | 9.9 | 1.17 | 11.7 | 1.21 | 12.1 | 1.42 | 14.2 |
| 3.00 | 1.07 | 10.7 | 1.26 | 12.6 | 1.30 | 13.0 | 1.53 | 15.3 |
| | Admix. Volume 150 mL | | | | Admix. Volume 100 mL | | | |
| | 100 mg/m$^2$ dose | | 120 mg/m$^2$ dose | | 100 mg/m$^2$ dose | | 120 mg/m$^2$ dose | |
| BSA (m$^2$) | BDM Conc (mg/ml) | % NA comp. | BDM Conc (mg/ml) | % NA comp. | BDM Conc (mg/ml) | % NA comp. | BDM Conc (mg/ml) | % NA comp. |
| 1.00 | 0.63 | 6.3 | 0.74 | 7.4 | 0.91 | 9.1 | 1.07 | 10.7 |
| 1.25 | 0.77 | 7.7 | 0.91 | 9.1 | 1.11 | 11.1 | 1.30 | 13.0 |

TABLE 3-continued

Concentrations of bendamustine (BDM, as HCl salt) and corresponding volume % of non-aqueous (NA) component in the final admixture, for volumes ranging from 100 ml to 250 ml For 10 mg/mL Formulation

| | | | | | | | | |
|---|---|---|---|---|---|---|---|---|
| 1.50 | 0.91 | 9.1 | 1.07 | 10.7 | 1.30 | 13.0 | 1.53 | 15.3 |
| 1.75 | 1.04 | 10.4 | 1.23 | 12.3 | 1.49 | 14.9 | 1.74 | 17.4 |
| 2.00 | 1.18 | 11.8 | 1.38 | 13.8 | 1.67 | 16.7 | 1.94 | 19.4 |
| 2.25 | 1.30 | 13.0 | 1.53 | 15.3 | 1.84 | 18.4 | 2.13 | 21.3 |
| 2.50 | 1.43 | 14.3 | 1.67 | 16.7 | 2.00 | 20.0 | 2.31 | 23.1 |
| 2.75 | 1.55 | 15.5 | 1.80 | 18.0 | 2.16 | 21.6 | 2.48 | 24.8 |
| 3.00 | 1.67 | 16.7 | 1.94 | 19.4 | 2.31 | 23.1 | 2.65 | 26.5 |

Example 3

The procedures of Example 2 are repeated except that the dose appropriate volume of the 10 mg/ml bendamustine solution is diluted into 250 ml of normal saline. The final concentration of bendamustine in the 250 ml volume container ranges from about 0.05 mg/ml to about 1.3 mg/ml.

Example 4

The approximately 100 ml bendamustine HCl infusion of Example 2 is administered to a patient in about 15 minutes.

Example 5

Bendamustine-containing compositions may be prepared by adding 5 mg/ml of thioglycerol to 90% polyethylene glycol 400 and 10% propylene glycol. As indicated in the Table 4 below, NaOH may be added in an amount sufficient to get apparent pH of greater than or equal to 6.5 as measured using the pH method outlined in the USP monograph for polyethylene glycol (PEG). Bendamustine is then added to the sample to a concentration of 25 mg/ml as indicated in Table 4 below.

TABLE 4

| Formulation |
|---|
| BDM - 25 mg/mL |
| Thioglycerol - 5 mg/mL |
| PEG 400:PG (90:10) |
| qs to 1 mL |
| BDM - 25 mg/mL |
| Thioglycerol - 5 mg/mL |
| PEG 400:PG (90:10) |
| qs to 1 mL |
| (PEG 400 Treated with NaOH) |

The compositions are then admixed with normal saline based on the total dose of bendamustine HCl which in turn is based on the patient body surface area (BSA) and the dosing regimen (100 mg/m$^2$ for CLL and 120 mg/m2 for NLL; although dose modifications of 90, 60, 50, and 25 mg/m$^2$ are possible, only the highest two dosing regimens are considered for illustrative purposes, as these result in the highest concentration of bendamustine during infusion). Table 5 below provides the final concentration of bendamustine (as the HCl salt) in the final admixture, for volumes ranging from 250 ml to 50 ml.

As seen in Table 5, the concentrations of bendamustine (as HCl salt) and the corresponding volume percent of non-aqueous component are well below the corresponding solubilities at room temperature as detailed in Table 1, for all admixture volumes up to 50 ml. For example, for a 2.0 m$^2$ (average) patient dosed at 120 mg/m$^2$, the final concentration of bendamustine HCl in a 50 ml admixture is 4.03 mg/ml. This is above the solubility of bendamustine HCl at both refrigerated and room temperature conditions in the absence of any non-aqueous components (1.175 mg/ml at 2-8° C. and 3.304-3.461 mg/ml at room temperature, as shown in Table 1 for 100% normal saline), as would be the case with the currently approved Treanda product, thereby precluding preparation and storage of a 50 ml admixture volume. However, the use of the non-aqueous bendamustine formulation described in this example results in the presence of 16.1% of the non-aqueous component in the final admixture, which improves the room temperature solubility to about 6.5 mg/ml (solubility of 6.554 mg/ml and 7.012 mg/ml with 15% non-aqueous component, as shown in Table 1). Therefore, the solubility with the non-aqueous formulation is well above the final concentration (of bendamustine HCl) of 4.03 mg/mL, allowing preparation and storage of the 100 ml admixture at room temperature conditions. Therefore, the non-aqueous formulation of bendamustine described in this example may be diluted into smaller infusion volumes ranging from 250 ml or less, with bendamustine continuing to remain in solution if maintained at room temperature. However, at refrigerated temperatures, the concentrations of bendamustine (as HCl salt) and the corresponding volume percent of non-aqueous component exceed the corresponding solubilities as detailed in Table 1, for all admixture volumes equal to or below 150 ml. In the scenario above, the solubility at refrigerated conditions with 15% non-aqueous component has improved to 2.9 mg/ml but is still below the final concentration of 4.03 mg/ml. Therefore, 50 ml admixtures of the non-aqueous formulation described in the example cannot be prepared and stored at refrigerated temperatures. However, for a 150 ml admixture, the final concentration of bendamustine HCl in this scenario is 1.5 mg/ml with about 6.0% non-aqueous component, which is below the solubility limit (of 2.022 mg/ml at 5% non-aqueous at 2-8° C.). Therefore, the non-aqueous formulation of bendamustine described in this example may be diluted into smaller infusion volumes ranging from 250 ml to 50 ml, and stored at only room temperature (but not refrigerated temperature), with bendamustine continuing to remain in solution. For storage at refrigerated temperatures, the minimum admixture volume that can be used is 150 ml or higher.

TABLE 5

Concentrations of bendamustine (BDM, as HCl salt) and corresponding volume % of non-aqueous (NA) component in the final admixture, for volumes ranging from 100 ml to 250 ml For 25 mg/mL Formulation

| | Admix. Volume 250 mL | | | | Admix. Volume 200 mL | | | |
|---|---|---|---|---|---|---|---|---|
| | 100 mg/m$^2$ dose | | 120 mg/m$^2$ dose | | 100 mg/m$^2$ dose | | 120 mg/m$^2$ dose | |
| BSA (m$^2$) | BDM Conc (mg/ml) | % NA comp. | BDM Conc (mg/ml) | % NA comp. | BDM Conc (mg/ml) | % NA comp. | BDM Conc (mg/ml) | % NA comp. |
| 1.00 | 0.39 | 1.6 | 0.47 | 1.9 | 0.49 | 2.0 | 0.59 | 2.3 |
| 1.25 | 0.49 | 2.0 | 0.59 | 2.3 | 0.61 | 2.4 | 0.73 | 2.9 |
| 1.50 | 0.59 | 2.3 | 0.70 | 2.8 | 0.73 | 2.9 | 0.87 | 3.5 |
| 1.75 | 0.68 | 2.7 | 0.81 | 3.3 | 0.85 | 3.4 | 1.01 | 4.0 |
| 2.00 | 0.78 | 3.1 | 0.92 | 3.7 | 0.96 | 3.8 | 1.15 | 4.6 |
| 2.25 | 0.87 | 3.5 | 1.04 | 4.1 | 1.08 | 4.3 | 1.28 | 5.1 |
| 2.50 | 0.96 | 3.8 | 1.15 | 4.6 | 1.19 | 4.8 | 1.42 | 5.7 |
| 2.75 | 1.05 | 4.2 | 1.25 | 5.0 | 1.30 | 5.2 | 1.55 | 6.2 |
| 3.00 | 1.15 | 4.6 | 1.36 | 5.4 | 1.42 | 5.7 | 1.68 | 6.7 |

| | Admix. Volume 150 mL | | | | Admix. Volume 100 mL | | | |
|---|---|---|---|---|---|---|---|---|
| | 100 mg/m$^2$ dose | | 120 mg/m$^2$ dose | | 100 mg/m$^2$ dose | | 120 mg/m$^2$ dose | |
| BSA (m$^2$) | BDM Conc (mg/ml) | % NA comp. | BDM Conc (mg/ml) | % NA comp. | BDM Conc (mg/ml) | % NA comp. | BDM Conc (mg/ml) | % NA comp. |
| 1.00 | 0.65 | 2.6 | 0.78 | 3.1 | 0.96 | 3.8 | 1.15 | 4.6 |
| 1.25 | 0.81 | 3.2 | 0.96 | 3.8 | 1.19 | 4.8 | 1.42 | 5.7 |
| 1.50 | 0.96 | 3.8 | 1.15 | 4.6 | 1.42 | 5.7 | 1.68 | 6.7 |
| 1.75 | 1.11 | 4.5 | 1.33 | 5.3 | 1.64 | 6.5 | 1.94 | 7.7 |
| 2.00 | 1.27 | 5.1 | 1.50 | 6.0 | 1.85 | 7.4 | 2.19 | 8.8 |
| 2.25 | 1.42 | 5.7 | 1.68 | 6.7 | 2.06 | 8.3 | 2.44 | 9.7 |
| 2.50 | 1.56 | 6.3 | 1.85 | 7.4 | 2.27 | 9.1 | 2.68 | 10.7 |
| 2.75 | 1.71 | 6.8 | 2.02 | 8.1 | 2.48 | 9.9 | 2.92 | 11.7 |
| 3.00 | 1.85 | 7.4 | 2.19 | 8.8 | 2.68 | 10.7 | 3.15 | 12.6 |

| | Admix. Volume 50 mL | | | |
|---|---|---|---|---|
| | 100 mg/m$^2$ dose | | 120 mg/m$^2$ dose | |
| BSA (m$^2$) | BDM Conc (mg/ml) | % NA comp. | BDM Conc (mg/ml) | % NA comp. |
| 1.00 | 1.85 | 7.4 | 2.19 | 8.8 |
| 1.25 | 2.27 | 9.1 | 2.68 | 10.7 |
| 1.50 | 2.68 | 10.7 | 3.15 | 12.6 |
| 1.75 | 3.07 | 12.3 | 3.60 | 14.4 |
| 2.00 | 3.45 | 13.8 | 4.03 | 16.1 |
| 2.25 | 3.81 | 15.3 | 4.44 | 17.8 |
| 2.50 | 4.17 | 16.7 | 4.84 | 19.4 |
| 2.75 | 4.51 | 18.0 | 5.22 | 20.9 |
| 3.00 | 4.84 | 19.4 | 5.59 | 22.4 |

Example 6

The hemolytic potential of the non-aqueous bendamustine formulation indicated in Table 4 (Example 5), when admixed with 250 ml and 100 ml of normal saline, was assessed. The hemolysis study was conducted at the highest final bendamustine HCl concentrations expected at these admixture volumes, namely, for a 3.0 m$^2$ patient dosed at 120 mg/m$^2$. At this dosing, the final bendamustine HCl concentration for 250 ml and 100 ml admixture volumes is 1.36 mg/ml and 3.15 mg/ml, respectively (Table 5). Human whole blood (1 ml) was incubated at 37° C. for approximately 30 minutes with admixed bendamustine HCl solutions at 1.4 mg/ml or 3.2 mg/ml at blood to drug solution volumetric ratios of 1:2 and 1:1, respectively. These volumetric ratios correspond to infusion times of 15 minutes and 10 minutes, respectively, for the 250 ml and 100 ml admixture volumes. A placebo of the bendamustine formulation (without the active ingredient) was also evaluated at these concentrations and volumetric ratios. A positive control (1% saponin solution), a negative control (normal saline), and Treanda™ diluted in normal saline to the highest concentration stated in the prescribing information (0.6 mg/ml) were included in the study. Following incubation and centrifugation of the samples, the plasma was harvested and hemolysis was evaluated by spectrophotometric analysis for hemoglobin in the supernatant. The results are summarized in Table 6. No hemolysis was observed with the non-aqueous bendamustine formulation when diluted with saline at either concentration or volumetric (blood:drug solution) ratios, or with the corresponding placebo at comparable sample volumes; supernatants from all samples were light yellow. In conclusion, no hemolytic effects are observed with non-aqueous bendamustine formulations when diluted to smaller volumes (100 to 250 ml) and infused in shorter times (10-15 minutes) than current practice.

TABLE 6

Hemolytic Potential test results

| Mixture | Hemoglobin[a] (mg/dL) | Test Result | Supernatant Color[b] | Tube No. |
|---|---|---|---|---|
| Human blood plus: | | | | |
| Test Article A | 1 | N | Light yellow | 1 |
| (25 mg/mL, diluted to | 0 | N | Light yellow | 2 |
| 3.2 mg/mL with saline) - | 1 | N | Light yellow | 3 |
| 100 ml admixture | | | | |
| Test Article A | 2 | N | Light yellow | 4 |
| (25 mg/mL, diluted to | 1 | N | Light yellow | 5 |
| 1.4 mg/mL with saline) - | 1 | N | Light yellow | 6 |
| 250 ml admixture | | | | |
| Test Article A Vehicle | 0 | N | Light yellow | 7 |
| (Placebo, diluted with | 1 | N | Light yellow | 8 |
| 100 ml saline) | 0 | N | Light yellow | 9 |
| Test Article A Vehicle | 1 | N | Light yellow | 10 |
| (Placebo, diluted with | 4 | N | Light yellow | 11 |
| 250 ml saline) | 1 | N | Light yellow | 12 |
| Treanda ™ | 3 | N | Light yellow | 43 |
| (5 mg/mL, diluted to | 4 | N | Light yellow | 44 |
| 0.6 mg/mL with saline) | 2 | N | Light yellow | 45 |
| Negative Control | 9 | N | Yellow | 55 |
| (normal saline) | 5 | N | Yellow | 56 |
| | 3 | N | Yellow | 57 |
| Positive Control | 5949 | P | Red | 58 |
| (1% Saponin)[c] | 5974 | P | Red | 59 |
| | 6386 | P | Red | 60 |

N = Negative, no hemolysis.
NA = Not applicable.
P = Positive, hemolysis.
[a]Hemoglobin index of the mixture supernatants.
[b]Plasma separated from whole blood plasma.
[c]1% Saponin. Saponin is a hemolytic agent used to lyse erythrocytes.

Example 7

The local tolerance (intravenous (IV) and perivascular (PV)) of the non-aqueous bendamustine-containing composition indicated in Table 4 (Example 5), when admixed with 100 ml of normal saline and infused over 10 minutes, was assessed. New Zealand White rabbits (3 males [IV] and 2 males [PV]) received a single dose of bendamustine formulation (admixed with 100 ml saline to a final concentration of 3.2 mg/ml bendamustine HCl) and corresponding placebo in the left and right ear, respectively. The formulation was administered as either intravenous infusion (5 mg/kg in 10 minutes), or perivascular injection (250 μl) to determine local tolerance. Treanda™ reconstituted and admixed with normal saline to a final concentration of 0.6 mg/ml (the highest concentration stated in the label) was also studied either as a 30 minute IV infusion (the shortest infusion time stated in the label), as well as perivascular injection (250 μl). Animals were held for a 96 hour (post-dose) observation period. During the observation period, dermal scores were recorded for all administration sites. At the end of the observation periods, animals were euthanized and a macroscopic and microscopic examination of both ears was performed. Parameters evaluated during the study were: viability, clinical observations, body weights, macroscopic observations and microscopic pathology.

The results of the local tolerance study are summarized in Table 7 (in life dermal observations) and Table 8 (microscopic pathology for perivascular administration).

In Life Dermal Observations:

As seen in Table 7, there was transient, dermal irritation in the form of slight to moderate erythema and moderate edema noted between 24 and 72 hours post dose, in each of the groups receiving either bendamustine-containing formulations or placebo material intravenously. At 96 hours, irritation was limited to a few individual sites treated with test or placebo articles. Only a limited number of animals were affected, and there was no consistent pattern of irritation within a dose group (either for test article or placebo). The bendamustine formulations were considered not to produce dermal irritation when administered intravenously.

Perivascular administration of bendamustine formulations (0.25 ml injection volume) produced dermal irritation in all groups. Local signs of dermal irritation following perivascular administration were mostly characterized by slight (group 6-Treanda™) or slight to moderate (group 7-non aqueous bendamustine formulation of example 5) erythema, and slight edema (groups 7). The severity of the irritation observed correlated with the dose and/or concentration of the test article administered, with placebo groups generally showing a lesser level of irritation than the corresponding test-article formulation.

TABLE 7

Summary of in life dermal observations

| Material - Left ear/Right ear | Left ear (Bendamustine-containing formulation) | Right ear (Placebo material) |
|---|---|---|
| Dermal observations during 96 hour post dose period (incidence and most severe level of erythema and edema noted) | | |
| Intravenous administration | | |
| Group 1: Treanda ™ diluted to 0.6 mg/ml in saline/Treanda Placebo - 500 ml admixture | — | (2/3) Slight |
| Group 2: Non-aqueous bendamustine formulation 25 mg/ml diluted to 3.2 mg/ml in saline/placebo (+saline) - 100 ml admixture | — | (1/3) Moderate |
| Perivascular administration | | |
| Group 6: Treanda ™ diluted to 0.6 mg/ml in saline/Treanda ™ Placebo - 500 ml admixture | (1/2) Slight | (1/2) Slight |
| Group 7: Non-aqueous bendamustine formulation 25 mg/ml diluted to 3.2 mg/ml in saline/placebo (+saline) - 100 ml admixture | (2/2) Moderate | (2/2) Slight |

Microscopic Pathology:

Intravenous administration of test articles/placebos was generally well tolerated; no test article related effects were observed. Perivascular administration of bendamustine-containing formulations (including Treanda™) was associated with dose and/or concentration related minimal to marked edema/collagen degeneration and mixed inflammation in perivascular tissues. The non-aqueous formulation of bendamustine (Group 7) was nominally more severe in grade than Treanda™ (Group 6).

TABLE 8

Incidence and Average Severity of Microscopic Findings at Perivascular Sites

| Formulation | Treanda ™ (diluted to 0.6 mg/ml)/ Treanda ™ Placebo | Non Aqueous Bendamustine (diluted to 3.2 mg/ml)/ Placebo |
|---|---|---|
| Group number | 6 | 7 |
| No. Animals examined | 2 | 2 |
| RIGHT EAR (RE) - Placebo | Incidence (Average Severity)* | |
| RE Injection site | | |
| Hemorrhage | 0 (0.0) | 0 (0.0) |
| Mixed Inflammation | 0 (0.0) | 0 (0.0) |
| Edema/Collagen Degeneration | 1 (0.5) | 0 (0.0) |
| Degeneration/Inflammation, Vascular | 0 (0.0) | 0 (0.0) |
| RE 2 cm distal | | |
| Edema/Collagen Degeneration | 0 (0.0) | 0 (0.0) |
| Degeneration/Inflammation, Vascular | 0 (0.0) | 0 (0.0) |
| RE 4 cm distal | | |
| Degeneration/Inflammation, Vascular | 0 (0.0) | 0 (0.0) |
| LEFT EAR (LE) - Test Article | Incidence (Average Severity) | |
| LE Injection site | | |
| Hemorrhage | 0 (0.0) | 0 (0.0) |
| Mixed inflammation | 0 (0.0) | 2 (2.0) |
| Edema/Collagen Degeneration | 1 (1.0) | 2 (1.5) |
| Epidermis, Crust/Pustule, Erosion/ Ulceration | 0 (0.0) | 0 (0.0) |
| Degeneration/Inflammation, Vascular | 1 (1.5) | 1 (1.5) |
| LE 2 cm distal | | |
| Hemorrhage | 0 (0.0) | 0 (0.0) |
| Mixed Inflammation | 1 (0.5) | 1 (1.0) |
| Edema/Collagen Degeneration | 0 (0.0) | 2 (2.0) |
| Epidermis, Crust/Pustule, Erosion/ Ulceration | 0 (0.0) | 0 (0.0) |
| Degeneration/Inflammation, Vascular | 0 (0.0) | 0 (0.0) |
| LE 4 cm distal | | |
| Hemorrhage | 0 (0.0) | 0 (0.0) |
| Mixed inflammation | 0 (0.0) | 1 (1.5) |
| Edema/Collagen Degeneration | 0 (0.0) | 1 (2.0) |
| Epidermis, Crust/Pustule, Erosion/ Ulceration | 0 (0.0) | 0 (0.0) |
| Degeneration/Inflammation, Vascular | 0 (0.0) | 0 (0.0) |

*The number in parentheses represents the average severity score; the total of severity scores of the findings divided by the number of animals in the group.

Conclusion:

No test-article related irritation effects were observed for the non-aqueous formulation of bendamustine via the IV route, indicating that proper administration of this formulation did not result in any adverse local reaction. Perivascular administration of the non-aqueous bendamustine formulation, which is primarily related to effects that may occur if extravasation should occur, resulted in irritation that was generally comparable to Treanda. Therefore, the non-aqueous formulation of bendamustine described herein is well tolerated, despite the higher concentration of the smaller infusion volume preparation.

Example 8

The chemical stability of the non-aqueous bendamustine formulation (25 mg/ml) indicated in Table 4 (Example 5), when admixed with 50 ml and 100 ml of normal saline, was assessed. For each admixture volume, the admixture solutions were prepared at the expected lowest concentration (corresponding to a 1.0 m$^2$ patient dosed at 25 mg/m$^2$) and the highest concentration (corresponding to a 3.0 m$^2$ patient dosed at 120 mg/m$^2$) of bendamustine HCl in the final admixture. For the 50 ml admixture volume, the tested minimum and maximum concentrations are about 0.5 mg/ml and 6.0 mg/ml, respectively. For the 100 ml admixture volume, the tested minimum and maximum concentrations are about 0.25 mg/ml and 3.2 mg/ml, respectively. The chemical stability of Treanda™ was also determined at the lowest (0.2 mg/ml) and the highest (0.6 mg/ml) admixed concentrations stated in the label. The chemical stability was monitored at room temperature at periodic intervals up to 24 hours using a validated HPLC assay. The results are summarized in Table 9.

TABLE 9

Dilution (Admixed) Stability of Bendamustine Formulations in Normal Saline at Room Temperature

| Attribute | Highest Concentration (3.2 mg/ml) | | | | | Lowest Concentration (0.25 mg/ml) | | | | |
|---|---|---|---|---|---|---|---|---|---|---|
| Time | Initial | 1 hr | 3 hrs | 6 hrs | 24 hrs | Initial | 1 hr | 3 hrs | 6 hrs | 24 hrs |
| Formulation | Non Aqueous Bendamustine Formulation 25 mg/ml admixed with 100 ml normal saline | | | | | | | | | |
| Assay (mg/ml) | 3.155 | 3.090 | 3.060 | 3.085 | 2.895 | 0.240 | 0.234 | 0.229 | 0.224 | 0.196 |
| Assay (% Initial) | 100.0 | 97.9 | 97.0 | 97.8 | 91.8 | 100.0 | 97.5 | 95.4 | 93.3 | 81.7 |
| Impurity - MCE (%) | BLQ | BLQ | BLQ | BLQ | BLQ | ND | ND | ND | ND | ND |
| Impurity - HP1 (%) | 0.244 | 0.606 | 1.237 | 2.236 | 6.707 | 0.525 | 1.449 | 3.495 | 5.529 | 13.424 |
| Impurity - Dimer (%) | BLQ | BLQ | BLQ | 0.068 | 0.158 | ND | ND | ND | BLQ | 0.063 |
| Single unknown (%) | 0.086 | 0.061 | BLQ | BLQ | 0.098 | ND | ND | ND | ND | BLQ |
| Total (%) | 0.33 | 0.67 | 1.24 | 2.30 | 6.96 | 0.58 | 1.45 | 3.50 | 5.53 | 13.49 |
| Attribute | Highest Concentration (6.4 mg/ml) | | | | | Lowest Concentration (0.5 mg/ml) | | | | |
| Time | Initial | 1 hr | hrs | 6 hrs | 24 hrs | Initial | 1 hr | 3 hrs | 6 hrs | 24 hrs |
| Formulation | Non Aqueous Bendamustine Formulation 25 mg/ml admixed with 50 ml normal saline | | | | | | | | | |
| Assay (mg/ml) | 6.62 | 6.60 | 6.60 | 6.54 | 6.46 | 0.475 | 0.470 | 0.455 | 0.445 | 0.394 |
| Assay (% Initial) | 100.0 | 99.7 | 99.7 | 98.8 | 97.8 | 100.0 | 98.9 | 95.8 | 93.7 | 82.9 |

TABLE 9-continued

Dilution (Admixed) Stability of Bendamustine Formulations in Normal Saline at Room Temperature

| Impurity - MCE (%) | BLQ | BLQ | BLQ | BLQ | 0.074 | BLQ | BLQ | BLQ | BLQ | BLQ |
|---|---|---|---|---|---|---|---|---|---|---|
| Impurity - HP1 (%) | 0.137 | 0.265 | 0.528 | 0.945 | 2.967 | 0.567 | 1.618 | 3.719 | 5.892 | 14.427 |
| Impurity - Dimer (%) | BLQ | BLQ | BLQ | 0.050 | 0.110 | BLQ | BLQ | BLQ | 0.065 | 0.115 |
| Single unknown (%) | 0.112 | 0.105 | 0.086 | 0.054 | 0.112 | 0.057 | BLQ | ND | ND | ND |
| Total (%) | 0.25 | 0.37 | 0.61 | 1.05 | 3.36 | 0.67 | 1.62 | 3.72 | 5.96 | 14.54 |

| Attribute | Highest Concentration (0.6 mg/ml) | | | | | Lowest Concentration (0.2 mg/ml) | | | | |
|---|---|---|---|---|---|---|---|---|---|---|
| Time | Initial | 1 hr | 3 hrs | 6 hrs | 24 hrs | Initial | 1 hr | 3 hrs | 6 hrs | 24 hrs |
| Formulation | Treanda™ 5 mg/ml admixed with 500 ml normal saline | | | | | | | | | |
| Assay (mg/ml) | 0.566 | 0.558 | 0.544 | 0.527 | 0.454 | 0.193 | 0.191 | 0.185 | 0.178 | 0.154 |
| Assay (% Initial) | 100.0 | 98.6 | 96.1 | 93.1 | 80.2 | 100.0 | 99.0 | 95.9 | 92.2 | 79.8 |
| Impurity - MCE (%) | 0.263 | 0.261 | 0.268 | 0.262 | 0.263 | 0.261 | 0.288 | 0.277 | 0.250 | 0.276 |
| Impurity - HP1 (%) | 1.250 | 2.248 | 4.730 | 7.287 | 16.887 | 1.231 | 2.241 | 4.770 | 7.462 | 17.504 |
| Impurity - Dimer (%) | 0.223 | 0.229 | 0.269 | 0.279 | 0.326 | 0.188 | 0.185 | 0.178 | 0.176 | 0.252 |
| Single unknown (%) | 0.103 | 0.103 | 0.101 | 0.097 | 0.081 | 0.077 | 0.079 | 0.103 | 0.083 | 0.066 |
| Total (%) | 1.97 | 2.97 | 5.50 | 8.04 | 17.66 | 1.85 | 3.01 | 5.41 | 8.07 | 18.27 |

MCE—monochloroethyl derivative;
HP1—mono hydroxyl bendamustine

As shown in Table 9, Treanda™ when prepared as directed in the label (final concentration between 0.2-0.6 mg/ml) shows total degradation of about 5-6% in 3 hours at room temperature (corresponding to the room temperature stability claim in the label); monohydroxy bendamustine is the main degradant. In contrast, the non-aqueous bendamustine formulations admixed in either 50 ml or 100 ml saline show total degradation of less than 5-6% over 6 hours at the lowest concentrations tested, indicating that these admixtures are significantly less prone to degradation. This stabilizing effect is particularly pronounced at the higher concentrations (which are more typical), with chemical stability evident for 24 hours at these concentrations. The non-aqueous formulations of bendamustine thus offer better chemical stability than Treanda™ when admixed into smaller volumes.

Example 9

Bendamustine-containing compositions were prepared by dissolving bendamustine HCl to a concentration of 10 mg/ml in one of ethanol, propylene glycol and benzyl alcohol as indicated in Table 10 below. 215 mg/ml of choline chloride was added in half of the samples as a source of soluble chloride ions. The samples were maintained at 40° C. and analyzed periodically for drug content and total impurities. The results obtained are presented in Table 10.

TABLE 10

Stability of Bendamustine HCl

| Formulation | Temp | Time | BDM mg/ml | % Total Impurities |
|---|---|---|---|---|
| BDM - 10 mg/mL | | Initial | 10.43 | 0.27 |
| Choline chloride - | 40° C. | 48 hrs | 10.48 | 1.27 |
| 215 mg/mL | | 7 day | 10.26 | 2.11 |
| Ethanol qs to 1 mL | | | | |
| BDM - 10 mg/mL | | Initial | 10.55 | 0.27 |
| Ethanol qs to 1 mL | 40° C. | 48 hrs | 10.30 | 2.39 |
| | | 7 day | 9.55 | 6.66 |
| BDM - 10 mg/mL | | Initial | 9.99 | 0.21 |
| Choline chloride - | 40° C. | 48 hrs | 9.95 | 0.60 |
| 215 mg/mL | | 7 day | 9.43 | 2.31 |
| Propylene glycol qs to 1 mL | | | | |
| BDM - 10 mg/mL | | Initial | 9.68 | 0.21 |
| Propylene glycol qs to 1 mL | 40° C. | 48 hrs | 9.45 | 0.88 |
| | | 7 day | 9.00 | 3.44 |
| BDM - 10 mg/mL | | Initial | 9.95 | 1.19 |
| Choline Chloride - | 40° C. | 48 hrs | 9.89 | 3.51 |
| 215 mg/mL | | 7 day | 8.97 | 4.24 |
| Benzyl alcohol qs to 1 mL | | | | |
| BDM - 10 mg/mL | | Initial | 9.52 | 0.33 |
| Benzyl alcohol qs | 40° C. | 48 hrs | 8.67 | 4.18 |
| to 1 mL | | 7 day | 7.49 | 7.84 |

Note:
In Table 10 the total % impurities include total contributions from peaks at various RRTs.

As shown in Table 10, the bendamustine formulations are very stable in solutions containing solvent and chloride salt. Table 10 shows that bendamustine, when dissolved at a concentration of about 10 mg/mL, in a pharmaceutically acceptable fluid, such as ethanol and propylene glycol, and containing a stabilizing amount of a chloride salt, such as choline chloride, had less than about 5% after at least 7 days storage at 40° C.

The data presented in Table 10 translates to bendamustine-containing compositions including a pharmaceutically acceptable fluid and a stabilizing amount of a chloride salt having a shelf life of at least about 15 months at 5° C. and 25° C.

The sample including ethanol alone exhibited more than 6.5 total degradants after 7 days storage at 40° C. The sample including benzyl alcohol alone exhibited more than 7.5% total degradants after 7 days storage at 40° C. Bendamustine-containing compositions with such high levels of degradation would not be suitable for long-term storage.

Example 10

Bendamustine-containing compositions were prepared by dissolving bendamustine HCl to a concentration of 10 mg/ml in DMSO. The samples were maintained at 40° C. and analyzed periodically for drug content and impurity profile. The results obtained are presented in Table 11.

TABLE 11

Stability of Bendamustine HCl in DMSO

| Formulation | Temp | Time | Content (mg/mL) | % Total Imp |
|---|---|---|---|---|
| BDM - 10 mg/mL | | Initial | 10.2 | 0.23 |
| DMSO qs to 1 mL | 40° C. | 48 hrs | 9.80 | 0.30 |
| | | 1 week | 10.0 | 0.56 |

Note:
In Table 11 the total % impurities include total contributions from peaks at various RRTs.

Table 11 shows that bendamustine, when dissolved in DMSO, had substantially no increase in total degradants. The data presented in Table 11 translates to bendamustine-containing compositions including DMSO having a shelf life of at least about 15 months at 5° C. and 25° C. In fact, such compositions are expected to have long term stability for periods beyond 15 months, i.e. up to 2 years or greater.

Example 11

Bendamustine-containing compositions were prepared by dissolving bendamustine HCl to a concentration of 20 mg/ml in polyethylene glycol 400 and 5 mg/ml of lipoic acid was added as a stabilizing antioxidant as indicated in Table 12 below. The samples were maintained at 40° C. or 25° C. and analyzed after 15 days for drug content and impurities. The results obtained are presented in Table 12.

TABLE 12

Stability of Bendamustine (20 mg/ml) in PEG 400 and Antioxidants

| Antioxidant | T° C. | Time days | % Initial | % Imp RRT 0.58 | % Total Imps |
|---|---|---|---|---|---|
| None | 25 | 15 | 97.6 | 2.08 | 2.28 |
| | 40 | 15 | 56.3 | 2.17 | 41.9 |
| Lipoic Acid | 25 | 15 | 98.5 | <LD | 0.23 |
| 5 mg/ml | 40 | 15 | 97.5 | 0.33 | 0.53 |

<LD = Below Level of Detection

As shown in Table 12, bendamustine, when dissolved in a pharmaceutically acceptable fluid, such as polyethylene glycol, in the presence of a stabilizing amount of an antioxidant, such as lipoic acid, had substantially no increase in total degradants after a period of 15 days. The data presented in Table 12 translates to bendamustine-containing compositions including a pharmaceutically acceptable fluid and a stabilizing amount of an antioxidant having a shelf life of at least about 15 months at 5° C. and 25° C.

The sample including PEG alone, on the other hand, which did not contain an antioxidant, did not exhibit stabilizing effects at 40° C. This sample had more than 40% more total impurities than the sample including lipoic acid. Bendamustine-containing compositions with such high levels of total impurities would not be suitable for long-term storage.

Example 12

Bendamustine-containing compositions were prepared by dissolving bendamustine HCl to a concentration of 50 mg/ml in 90% polyethylene glycol 400 and 10% propylene glycol. 5 mg/ml of thioglycerol, α-lipoic acid or dihydrolipoic acid was added as a stabilizing antioxidant as indicated in Table 13 below. The samples were maintained at 40° C. and analyzed after 15 days or one month for drug content and impurity profile as indicated in Table 13 below. The results obtained are presented in Table 13.

TABLE 13

Stability of Bendamustine (50 mg/ml) in 90% PEG 400, 10% Propylene Glycol and Antioxidant

| | | | | | % Impurities RRT | | |
|---|---|---|---|---|---|---|---|
| Antioxidant | T (° C.) | Time | Content (mg/mL) | % Initial | HP1 0.59 | PG ester 1.10 | % Total Imps |
| Thioglycerol | 40 | initial | 48.8 | 100 | <LD | <LD | 0 |
| | 40 | 1 month | 48.5 | 99.4 | 0.06 | 0.20 | 0.71 |
| α-lipoic acid | 40 | initial | 49 | 100 | <LD | <LD | 0 |
| | 40 | 15 days | 48.8 | 99.6 | 0.19 | 0.13 | 0.32 |
| | 40 | 1 month | 48.7 | 99.4 | 0.34 | 0.26 | 0.79 |
| Dihydrolipoic | 40 | initial | 49.3 | 100 | <LD | <LD | 0 |
| acid | 40 | 1 month | 47.7 | 97.4 | 0.63 | 0.12 | 1.84 |

<LD = Below Level of Detection

As shown in Table 13, bendamustine, when dissolved in a pharmaceutically acceptable fluid, such as a combination of polyethylene glycol and propylene glycol, in the presence of a stabilizing amount of an antioxidant, such as thioglycerol, α-lipoic acid or dihydrolipoic acid, had substantially no increase in total degradants after a period of 1 month. This data supports the position that bendamustine-containing compositions according to the invention have a shelf life of at least about 2 years when stored at temperatures between 5° C. and 25° C.

Example 13

Bendamustine-containing compositions were prepared by dissolving bendamustine HCl to a concentration of 50 mg/ml in a mixture of polyethylene glycol 400 and propylene glycol as indicated in Table 14 below. 5 mg/ml of lipoic acid was added as a stabilizing antioxidant. The samples were maintained at 40° C., 25° C. and 5° C. and analyzed after 1 week, 15 days or one month for drug content and impurity profile as indicated in Table 14 below. The results obtained are presented in Table 14.

TABLE 14

Stability of Bendamustine (50 mg/ml) and Lipoic Acid (5 mg/ml) in PEG400 and Propylene glycol

| | | | | | % Area of degradants | | | % |
|---|---|---|---|---|---|---|---|---|
| Formulation | Temp. | Time Period | Content (mg/mL) | % of Initial | HP1 0.58 | PG ester 1.10 | PG ester 1.13 | Total Imp. |
| BDM - | | Initial | 49.6 | 100 | BDL | BDL | BDL | 0.18 |
| 50 mg/mL | 40 °C. | 1 W | 49.0 | 98.8 | 0.05 | 0.13 | BDL | 0.38 |
| Lipoic acid - | | 15 d | 48.3 | 97.4 | 0.08 | 0.26 | BDL | 0.55 |
| 5 mg/mL | | 1 M | 48.0 | 96.8 | 0.11 | 0.43 | 0.13 | 1.03 |
| PEG | 25° C. | 15 d | 49.6 | 100.0 | BDL | 0.10 | BDL | 0.30 |
| 400:PG | | 1 M | 48.4 | 97.6 | 0.05 | 0.19 | BDL | 0.43 |
| (75:25) qs | 5° C. | 1 M | 49.6 | 100.0 | BDL | 0.07 | BDL | 0.27 |
| to 1 mL | | | | | | | | |
| BDM - | | Initial | 50.2 | 100 | BDL | BDL | BDL | 0.21 |
| 50 mg/mL | 40 °C. | 1 W | 49.9 | 99.4 | BDL | 0.15 | BDL | 0.30 |
| Lipoic acid - | | 15 d | 49.1 | 97.8 | 0.06 | 0.35 | BDL | 0.73 |
| 5 mg/mL | | 1 M | 49.0 | 97.6 | 0.09 | 0.90 | 0.25 | 1.82 |
| PEG | 25° C. | 15 d | 49.9 | 99.4 | BDL | 0.12 | BDL | 0.32 |
| 400:PG | | 1 M | 49.7 | 99.0 | BDL | 0.25 | BDL | 0.59 |
| (50:50) qs | 5° C. | 1 M | 50.0 | 99.6 | BDL | 0.11 | BDL | 0.33 |
| to 1 mL | | | | | | | | |
| BDM - | | Initial | 50.8 | 100 | BDL | BDL | BDL | 0.21 |
| 50 mg/mL | 40 °C. | 1 W | 50.4 | 99.2 | BDL | 0.11 | BDL | 0.30 |
| Lipoic acid - | | 15 d | 49.7 | 97.8 | 0.07 | 0.17 | BDL | 0.43 |
| 5 mg/mL | | 1 M | 49.7 | 97.8 | 0.13 | 0.27 | 0.09 | 0.84 |
| PEG | 25° C. | 15 d | 50.8 | 100.0 | BDL | 0.10 | BDL | 0.26 |
| 400:PG | | 1 M | 50.8 | 100.0 | 0.05 | 0.14 | BDL | 0.39 |
| (90:10) qs | 5° C. | 1 M | 50.8 | 100.0 | BDL | 0.06 | BDL | 0.34 |
| to 1 mL | | | | | | | | |

BDL = Below Detectable Limit

As shown in Table 14, bendamustine, when dissolved in certain mixtures of polyethylene glycol and propylene glycol and a stabilizing amount of lipoic acid, had substantially no increase in total degradants after a period of 1 month. The data presented in Table 14 translates to bendamustine-containing compositions having a shelf life of at least about 2 years when stored at temperatures between 5° C. and at 25° C.

Example 14

Bendamustine-containing compositions were prepared by dissolving bendamustine HCl to a concentration of 50 mg/ml in 90% polyethylene glycol 400 and 10% propylene glycol and α-lipoic acid was added as a stabilizing antioxidant as indicated in Table 15 below. The samples were maintained at 40° C., 25° C. and 5° C. and analyzed for drug content and impurity profile as indicated in Table 15 below. The results obtained are presented in Table 15.

TABLE 15

Stability of Bendamustine in 90% PEG 400, 10% PG and α-lipoic acid

| Formulation | Temp | Time Per. | Amt. mg/ml | % of Initial | % Area of degradants | | | | | | | | % Total Imp. |
|---|---|---|---|---|---|---|---|---|---|---|---|---|---|
| | | | | | 0.59 | 1.10 | 1.13 | 1.15 | 1.17 | 1.20 | 1.22 | 1.30 | |
| BDM - | | Initial | 51.0 | 100 | 0.20 | 0.06 | <LD | <LD | <LD | <LD | <LD | <LD | 0.26 |
| 50 mg/mL | 40° C. | 1 M | 50.5 | 99.0 | 0.21 | 0.31 | 0.13 | 0.07 | 0.13 | 0.10 | <LD | <LD | 0.95 |
| α-lipoic | | 2 M | 49.7 | 97.5 | 0.22 | 0.71 | 0.28 | 0.14 | 0.12 | 0.21 | 0.12 | <LD | 2.02 |
| acid - | | 3 M | 48.7 | 95.5 | 0.22 | 1.01 | 0.45 | 0.21 | 0.14 | 0.37 | 0.16 | 0.05 | 2.96 |
| 10 mg/mL | 25° C. | 3 M | 50.5 | 99.0 | 0.20 | 0.36 | 0.07 | <LD | <LD | 0.10 | <LD | <LD | 0.73 |
| PEG | | 6 M | 50.4 | 98.8 | 0.22 | 0.60 | 0.17 | 0.06 | 0.06 | 0.09 | 0.10 | 0.08 | 1.44 |
| 400:PG | 5° C. | 6 M | 50.9 | 99.8 | 0.16 | 0.05 | <LD | <LD | <LD | <LD | <LD | <LD | 0.21 |
| (90:10) qs | | 12 M | 50.6 | 99.2 | 0.20 | 0.18 | <LD | <LD | <LD | <LD | <LD | <LD | 0.38 |
| to 1 mL | | | | | | | | | | | | | |
| BDM - | | Initial | 50.3 | 100 | 0.18 | <LD | <LD | <LD | <LD | <LD | <LD | <LD | 0.18 |
| 50 mg/mL | 40° C. | 1 M | 50.0 | 99.4 | 0.19 | 0.32 | 0.08 | 0.06 | 0.08 | 0.06 | 0.06 | <LD | 0.85 |
| α-lipoic | | 2 M | 49.8 | 99.0 | 0.19 | 0.65 | 0.21 | 0.12 | 0.13 | 0.23 | 0.14 | 0.06 | 1.85 |
| acid - | | 3 M | 49.5 | 98.4 | 0.19 | 0.89 | 0.37 | 0.17 | 0.13 | 0.32 | 0.10 | <LD | 2.40 |
| 15 mg/mL | | 6 M | 47.0 | 93.4 | 0.20 | 1.76 | 0.66 | 0.19 | 0.31 | 0.47 | 0.33 | 0.17 | 4.93 |
| PEG | 25° C. | 3 M | 50.0 | 99.4 | 0.20 | 0.35 | 0.08 | <LD | <LD | <LD | 0.11 | <LD | 0.79 |
| 400:PG | | 6 M | 49.5 | 98.4 | 0.19 | 0.58 | 0.15 | 0.06 | 0.07 | 0.09 | 0.08 | 0.10 | 1.38 |
| (90:10) qs | 5° C. | 6 M | 50.3 | 100 | 0.17 | 0.06 | <LD | <LD | <LD | <LD | <LD | <LD | 0.23 |
| to 1 mL | | 12 M | 50.2 | 99.8 | 0.19 | 0.15 | <LD | <LD | <LD | <LD | <LD | <LD | 0.34 |

<LD = Below Level of Detection

The data reported in Table 15 along with the data in Table 14 demonstrates that bendamustine solutions are stable when dissolved in mixtures of PEG and PG and 5-15 mg/mL α-lipoic acid. As shown in Table 15, bendamustine, when dissolved in combinations of polyethylene glycol and propylene glycol, in the presence of a stabilizing amount of lipoic acid, had less than 3% increase in total degradants after a period of 3 months at 40° C. Additionally, the same compounds had substantially no increase in total degradants after a period of 6-12 months at 5° C. and 25° C. The data corresponds to bendamustine solutions being stable under ambient or refrigerated storage conditions for well in excess of 2 years, and thus long term stable.

Example 15

Bendamustine-containing compositions were prepared by dissolving bendamustine HCl to a concentration of 50 mg/ml in 90% polyethylene glycol 400 and 10% propylene glycol. 2.5 mg/ml of thioglycerol was added as an antioxidizing agent. The samples were maintained at 40° C. and 25° C. and analyzed for drug content and impurity profile as indicated in Table 16 below. The results obtained are presented in Table 16.

TABLE 16

Stability of Bendamustine in 90% PEG 400, 10% PG and Thioglycerol

| Formulation | Temp | Time Per. | Amt mg/ml | % of Initial | 0.15 | 0.37 | 1.10 | 1.13 | 1.15 | 1.17 | 1.18 | 1.20 | 1.22 | % Total Imp. |
|---|---|---|---|---|---|---|---|---|---|---|---|---|---|---|
| BDM - 50 mg/mL Thioglycerol - 2.5 mg/mL PEG 400:PG (90:10) qs to 1 mL | | Initial | 50.3 | 100 | BDL | BDL | BDL | BDL | BDL | BDL | BDL | BDL | BDL | 0.00 |
| | 40° C. | 15 d | 50.2 | 99.8 | BDL | BDL | 0.18 | BDL | BDL | BDL | 0.05 | 0.08 | BDL | 0.31 |
| | | 1 M | 49.9 | 99.2 | BDL | 0.12 | 0.32 | 0.07 | BDL | BDL | 0.09 | 0.08 | BDL | 0.75 |
| | | 2 M | 49.1 | 97.6 | BDL | 0.18 | 0.56 | 0.24 | 0.09 | 0.17 | 0.19 | 0.12 | 0.11 | 1.76 |
| | | 3 M | 48.8 | 97.0 | BDL | 0.23 | 0.85 | 0.34 | 0.16 | 0.30 | 0.34 | 0.29 | 0.19 | 2.94 |
| | 25° C. | 3 M | 49.9 | 99.2 | 0.06 | 0.12 | 0.23 | 0.07 | BDL | 0.06 | 0.07 | 0.06 | BDL | 0.67 |
| | | 6 M | 49.3 | 98.0 | BDL | 0.23 | 0.53 | 0.22 | 0.11 | BDL | 0.21 | 0.22 | 0.20 | 2.07 |

BDL = Below Detectable Limit

The stability is similar to that of α-lipoic acid samples in Example 14 above. As shown in Table 16, bendamustine, when dissolved in a combination of polyethylene glycol and propylene glycol, and a stabilizing amount of thioglycerol, had less than 3% increase in total degradants after a period of 3 months at 40° C. Additionally, the same compounds had substantially no increase in total degradants after a period of 6 months at 25° C. The data reported supports the conclusion that these bendamustine solutions are stable under ambient or refrigerated storage conditions for about 2 years.

Example 16

Bendamustine-containing compositions were prepared by dissolving bendamustine HCl to a concentration of 50 mg/ml in 85% PEG 400 and 15% PG in the presence of 5 mg/ml of thioglycerol. The samples were maintained at 40° C. and 25° C. and analyzed for drug content and impurity profile as indicated in Table 17 below. The results obtained are presented in Table 17.

TABLE 17

Stability of Bendamustine in 85% PEG 400, 15% PG and Thioglycerol

| Formulation | Temp. | Time Period | Content (mg/mL) | % of Initial | % Total Imp. |
|---|---|---|---|---|---|
| BDM - 50 mg/mL Thioglycerol - 5 mg/mL PEG 400:PG (85:15) qs to 1 mL | Initial | | 51.5 | 100 | 0.12 |
| | 40° C. | 1 M | 50.4 | 97.9 | 1.18 |
| | 25° C. | 1 M | 51.4 | 99.8 | 0.41 |
| | | 3 M | 50.4 | 97.9 | 1.21 |
| | 5° C. | 3 M | 51.0 | 99.0 | 0.26 |

The stability is similar to that of thioglycerol samples in Example 15 above. As reported in Table 17, total impurities did not exceed 2% at 40° C. or 25° C. storage over one month, or at 25° C. and 5° C. storage after three months. The data reported in Table 17 supports the conclusion that these bendamustine solutions are stable under ambient or refrigerated storage conditions for at least about 2 years if not longer.

I claim:

1. A method of treating chronic lymphocytic leukemia or indolent B cell non-Hodgkin's lymphoma in a subject comprising:
   a. providing a non-aqueous liquid composition comprising from about 10 mg/mL to about 100 mg/mL of bendamustine or a pharmaceutically acceptable salt thereof, wherein the total impurities are less than about 5% as determined by HPLC at a wavelength of 223 nm after 15 months at a temperature of from about 5° C. to about 25° C.;
   b. diluting said non-aqueous liquid composition with a parenterally acceptable aqueous diluent; and
   c. parenterally administering said diluted composition to the subject at a bendamustine dosage ranging from about 25 mg/m$^2$ to about 120 mg/m$^2$, wherein said administering step is performed with a total volume of about 100 mL or less of the diluted composition administered over a period of less than or equal to about 15 minutes.

2. The method of claim 1, wherein the non-aqueous liquid composition comprises a pharmaceutically acceptable fluid comprising polyethylene glycol, propylene glycol, ethanol, benzyl alcohol, glycofurol, or DMSO, or a mixture thereof.

3. The method of claim 1, wherein the non-aqueous liquid composition comprises polyethylene glycol, propylene glycol, or a mixture thereof.

4. The method of claim 1, wherein the non-aqueous liquid composition comprises DMSO.

5. The method of claim 1, wherein the non-aqueous liquid composition comprises ethanol.

6. The method of claim 1, wherein the non-aqueous liquid composition comprises benzyl alcohol.

7. The method of claim 1, wherein the non-aqueous liquid composition comprises glycofurol.

8. The method of claim 1, wherein the subject is a human.

9. The method of claim 1, wherein the concentration of the bendamustine or pharmaceutically acceptable salt thereof in said diluted composition is from about 0.05 to about 12.5 mg/mL.

10. The method of claim 1, wherein the concentration of the bendamustine or pharmaceutically acceptable salt thereof in said diluted composition is from about 0.1 to about 6.0 mg/mL.

11. The method of claim 1, wherein the concentration of the bendamustine or pharmaceutically acceptable salt thereof in said diluted composition is from about 0.05 to about 3.2 mg/mL.

12. The method of claim 1, wherein the concentration of the bendamustine or pharmaceutically acceptable salt thereof in said diluted composition is from about 0.5 to about 5.6 mg/mL.

13. The method of claim 8, wherein the volume administered is about 50 mL.

14. The method of claim 1, wherein long term storage stable non-aqueous liquid composition further comprises a stabilizing amount of an antioxidant.

15. The method of claim 14, wherein the antioxidant is selected from the group consisting of thioglycerol, monothioglycerol, lipoic acid, propyl gallate, methionine, cysteine, metabisulfites, sodium formaldehyde sulfoxylate, phenol-containing aromatic and aliphatic compounds and dihydrolipoic acid.

16. The method of claim 1, wherein the subject is being treated for chronic lymphocytic leukemia.

17. The method of claim 16, wherein the diluted composition is administered intravenously in a volume of about 50 mL in about 10 minutes or less on days 1 and 2 of a 28 day cycle.

18. The method of claim 17, wherein the diluted composition is administered in about 10 minutes.

19. The method of claim 17, wherein the method is repeated for up to 6 cycles.

20. The method of claim 16, wherein the subject is administered a bendamustine dosage amount ranging from about 25 mg/m$^2$ to about 100 mg/m$^2$.

21. The method of claim 20, wherein the bendamustine dosage amount is about 100 mg/m$^2$.

22. The method of claim 16, wherein the diluted composition comprises from about 1.85 mg/mL to about 4.84 mg/mL of bendamustine or a pharmaceutically acceptable salt thereof.

23. The method of claim 1, wherein the bendamustine is administered to treat indolent B cell non-Hodgkin's lymphoma.

24. The method of claim 23, wherein the diluted composition is administered intravenously in a volume of about 50 mL in about 10 minutes or less on days 1 and 2 of a 21 day cycle.

25. The method of claim 24, wherein the diluted composition is administered in about 10 minutes.

26. The method of claim 24, wherein the method is repeated for up to 8 cycles.

27. The method of claim 23, wherein the subject is administered a bendamustine dosage amount ranging from about 60 mg/m$^2$ to about 120 mg/m$^2$.

28. The method of claim 23, wherein the subject is administered a bendamustine dosage amount of about 120 mg/m$^2$.

29. The method of claim 28, wherein the diluted liquid composition comprises from about 2.19 mg/mL to about 5.59 mg/mL of bendamustine or a pharmaceutically acceptable salt thereof.

* * * * *